United States Patent [19]
Monroe et al.

[11] Patent Number: 5,347,989
[45] Date of Patent: Sep. 20, 1994

[54] CONTROL MECHANISM FOR STEERABLE ELONGATED PROBE HAVING A SEALED JOYSTICK

[75] Inventors: Richard A. Monroe, Liverpool; Jeffrey Perkins, Tully; Robert J. Wood, Syracuse, all of N.Y.

[73] Assignee: Welch Allyn, Inc., Skaneateles Falls, N.Y.

[21] Appl. No.: 943,929

[22] Filed: Sep. 11, 1992

[51] Int. Cl.[5] .................................. A61B 1/00
[52] U.S. Cl. ........................ 128/4; 200/302.3
[58] Field of Search .............. 128/4, 6; 273/438; 341/20, 21; 200/6 A, 302.1, 302.3, 5 R, 17 R; 74/471 XY

[56] References Cited

U.S. PATENT DOCUMENTS

| | | | |
|---|---|---|---|
| 4,414,438 | 11/1983 | Maier et al. | 200/6 A |
| 4,488,017 | 12/1984 | Lee | 200/5 R |
| 4,503,842 | 3/1985 | Takayama | 128/4 |
| 4,742,818 | 5/1988 | Hughes et al. | 128/6 |
| 4,789,766 | 12/1988 | Krause | 200/302.3 |
| 4,802,461 | 2/1989 | Cho | 128/7 |
| 4,941,454 | 7/1990 | Wood et al. | 128/4 |

Primary Examiner—Richard J. Apley
Assistant Examiner—John Mulcahy
Attorney, Agent, or Firm—Harris Beach & Wilcox

[57] ABSTRACT

A control handle for a video probe that includes a joystick mounted in a housing which is coupled to a stepper mechanism for moving the control cables of an elongated insertion tube in response to the manipulation by an operator. The joystick is sealed against liquid infiltration.

7 Claims, 3 Drawing Sheets

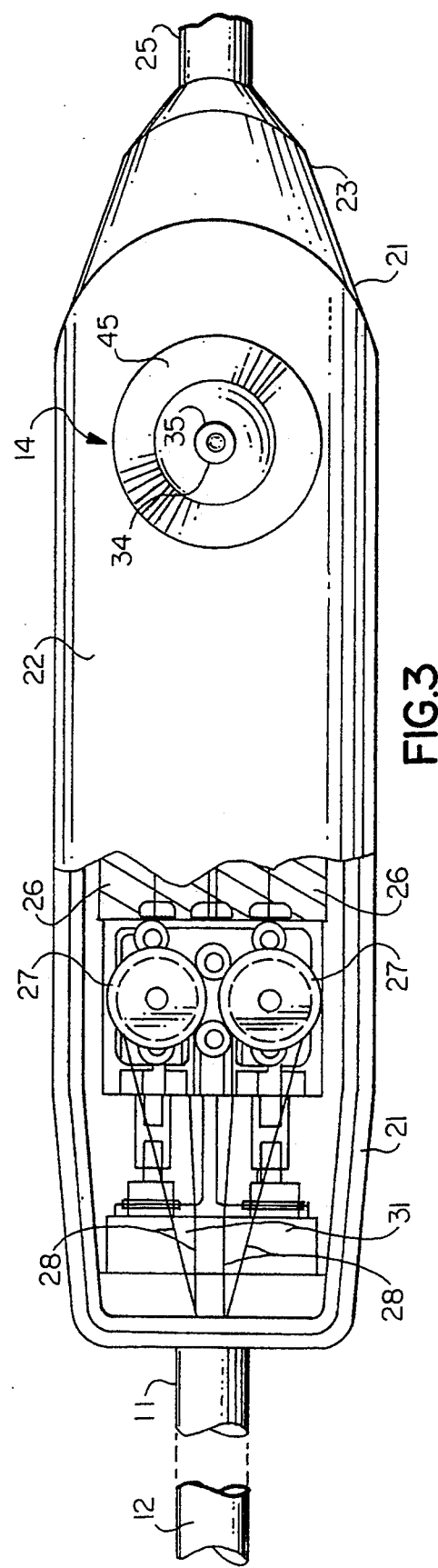
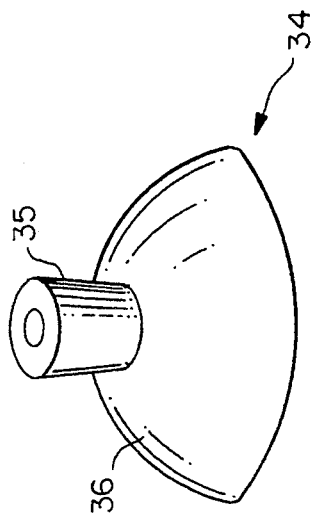
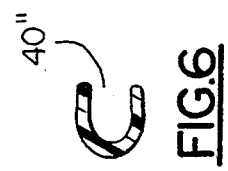
FIG.3
FIG.4
FIG.5
FIG.6

CONTROL MECHANISM FOR STEERABLE ELONGATED PROBE HAVING A SEALED JOYSTICK

BACKGROUND OF THE INVENTION

This invention relates to borescopes or endoscopes of the type in which an imager is mounted onto an elongated insertion tube for viewing a concealed target. The invention is more particularly concerned with probes of the type in which a flexible bendable distal tip is remotely steered by manipulation of a control mechanism.

Recently, interest has increased in the use of video instruments for surgical applications to permit a surgeon to carry out a procedure with minimal intervention in the patient. An example of one such video instrument is a laparoscope for performing surgery in the abdominal cavity, where the instrument is inserted through a small incision. Other probes are provided for diagnosis of medical conditions in the colon or in the gastro-enteric tract. Small probes can also be used in eye surgery. Further examples are found in industrial probes, i.e., borescopes, for inspection of equipment such as boilers or steam generators, or of jet engine rotors where non-destructive penetration of the equipment is necessary.

A laparoscope generally has a rigid metal insertion tube for insertion into the patient's body cavity. In a video type laparoscope there is a miniature camera contained in the distal tip of the insertion tube, with a small focusing lens system and a small solid state imager.

In many cases it is desirable to manipulate only the distal end of the tube when inserted within a patient.

Articulated flexible steering sections have often been employed with flexible probes, and many of these have been employed as cable driven steering sections. One successful system employs so-called wobble washers, that is, a series of rings which are separated by beads or spaces, and through which steering cables pass. An example of such a wobble-washer steering system is described in U.S. Pat. No. 4,700,693. These can be arranged for two-way steering (left-to-right and right-to-left) or four way steering (up-down and down-up as well). Four steering cables are employed, two for the left and right directions and two for the up and down directions. The cables pass from the articulated steering section proximally through the insertion tube to a control mechanism within a control housing. The cables of each pair are moved reciprocally. However, it is desirable to include a tension absorbing mechanism in the housing to accommodate strain on the cables resulting from steering. This occurs because the cable path lengths do change slightly as the steering section bends.

It is also desired to make control of steering responsive and to reduce the resistance felt by the surgeon or other operator on the control handle. Another problem was to provide one-hand control of both horizontal and vertical steering, without making the control mechanism cumbersome or uncomfortable, but to accomplish this in a sealed manner which would permit disinfection and sterilization of the device.

OBJECTS AND SUMMARY OF THE INVENTION

It is an object of this invention to provide a steerable, part rigid/part flexible laparoscope or other probe which avoids the problems of the prior art, and which permits one-hand joy stick steering, both horizontally and vertically.

It is another object to provide an environmentally sealed steering control mechanism which is convenient to use and which permits sterilization by immersion in an antiseptic medium, such as ethylene oxide.

In accordance with an aspect of this invention, a video laparoscope or other probe of that general type has an insertion tube in which the distal portion is articulated for remote steering both up and down and side to side. A steering control handle is attached to the proximal end of the insertion tube, and has a joystick or equivalent one-hand control for bending the articulated steering portion. A flexible umbilical connects the control handle to a plug-in modular connector that fits into a socket in a light and power supply unit. The umbilical carries a fiber optic light conduit that receives light from the light and power unit and which continues through the handle and insertion tube to the distal tip, from which light projects forward to illuminate the target. The umbilical also contains conductors that carry power and synchronizing signals to the video camera in the insertion tube tip, and which bring the video signal from the camera through the handle and umbilical to the modular connector. The signals are supplied to a video monitor to permit on-screen viewing of the surgical procedure as viewed by the miniature video camera.

The joystick mechanism includes a wineglass-shaped member, formed of a stem and a generally hemispheric bowl member which fits against a sealing ring that surrounds an opening in the handle housing. The sealing ring is a low-friction polymer, such as PTFE, so that a good seal is provided between the housing and the wineglass bowl member, but there is low frictional resistance to movement of the stem, which serves as a lever.

For each pair of steering cables, a stepper motor is provided.

The above and many other objects, features, and advantages of this invention will become apparent from the ensuing description of a preferred embodiment, which is to be read in conjunction with the accompanying Drawing.

BRIEF DESCRIPTION OF THE DRAWING

FIG. 3 is a top view, partly cut away, of the control handle portion of FIG. 2.

FIG. 4 is a detail perspective showing the wineglass shaped member of this embodiment.

FIGS. 5 and 6 are cross sections of sealing rings which can be employed with embodiments of this invention.

DETAILED DESCRIPTION OF THE PREFERRED EMBODIMENT

Figure 1:
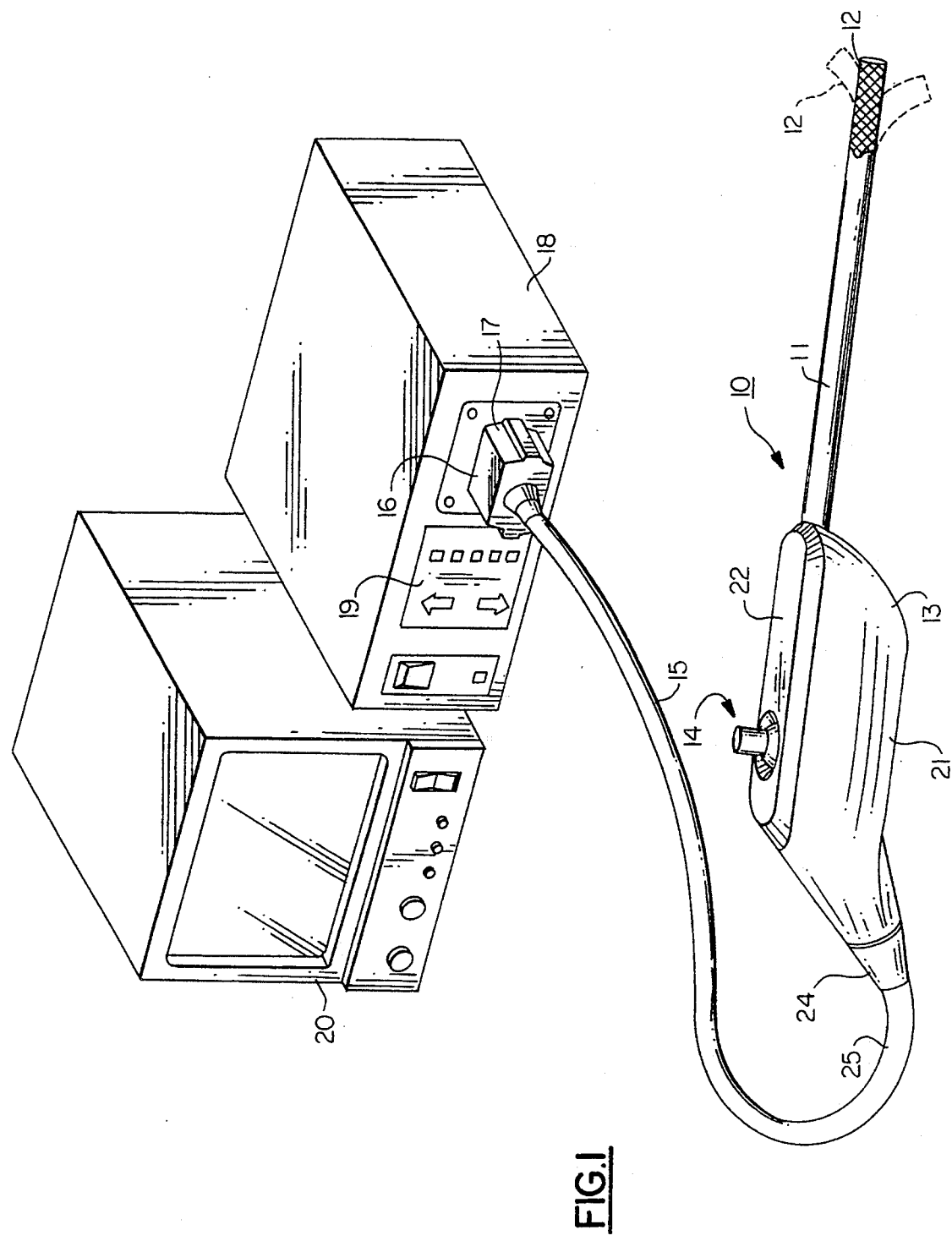
FIG. 1 is a perspective view of a steerable laparoscope according to one embodiment of this invention.

With reference to the Drawing, and initially to FIG. 1 thereof, a steerable laparoscope assembly 10 has an elongated insertion tube 11 which is rigid except for a flexible or bendable steering section 12 at its distal tip. While a variety of bending mechanisms are available for this section 12, the present embodiment employs a wobble washer system as described, for example, in U.S. U.S. Pat. No. 4,700,693 which is incorporated herein by reference. In such a steering section, there are two pairs of cables, one pair being moved differentially to bend the section sideways (i.e., in the x direction), and the other pair being moved differentially to bend the section vertically (i.e., in the y direction). The cables extend proximally within the insertion tube to a control mechanism that is housed within a control handle 13 to which the proximal end of the insertion tube is affixed. Here, a joystick control 14 permits one-hand simultaneous control of steering both horizontally and vertically.

The control handle 13 is coupled through a flexible umbilical tube 15 to a plug-in connector module 16. The latter contains electronic circuitry that provide appropriate power levels and synchronizing signals to a miniature video camera situated at the distal tip of the bending section 12. The circuitry in the connector module 16 also receives image signals from the miniature camera, which it uses to produce a standard video signal. The module 16 is removably inserted into a socket 17 of a lighting and power supply unit 18, an example of which is described in copending patent application Ser. No. 07/944,221, filed Sep. 11, 1992, and having a common assignee herewith. Situated on a front panel of the unit is a control panel 19 containing various control switches and indicators. A video monitor 20 provides a video picture of a target in the viewing path of the camera contained in the insertion tube 11.

Figure 2:
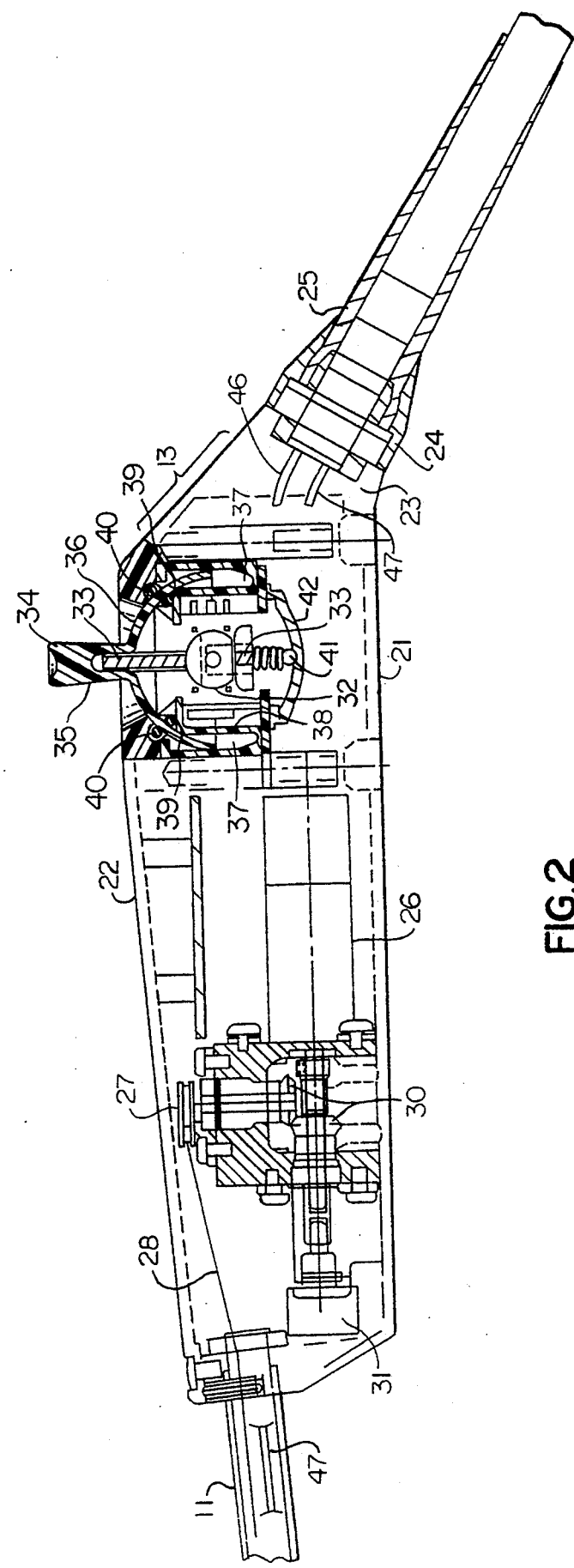
FIG. 2 is a sectional elevation of the control handle portion of the embodiment of FIG. 1.

As shown in greater detail in FIGS. 2 and 3, the control handle 13 is formed of a housing lower part 21, and a housing cover or upper part 22. These two housing parts 21, 22 are preferably formed of an aluminum alloy or other lightweight material, and define a hollow interior space. The housing is shaped to fit comfortably in the hands of a surgeon or other practitioner. A rear tapered portion 23 of the housing lower part 21 is connected by a threaded connector 24 to a strain relief 25 associated with the distal end of the umbilical 15.

A pair of stepper device or other actuators are located side by side within the lower housing 21 and each is connected to rotatable pivot wheels 27 through a set of bevelled gears 30. An associated pair of steering cables 28 is connected to the pivot wheels 27, deflect the flexible distal tip sideways or vertically when the pivot wheel 27 is rotated.

A single turn potentiometer 31 is mounted to each of the stepper motors drive shaft extensions and serves to indicate the position of the motor shafts and the rotatable pivot wheels. A position control drives the stepper motors 26 until the potentiometer signal matches the signal from the joystick.

The stepper motors 26 enjoy limited fore-and-aft travel on respective tracks (not shown) and resilient biasing springs (not shown) are positioned to absorb overtension on the cables 28.

As also shown in FIGS. 2 and 3, the joystick control 14 for controlling the steering cables 28 comprises an x-y joystick dual potentiometer switch mechanism 32 or element having a control lever 33. A "wineglass" control handle member 34 for manipulating the joystick switch mechanism 32 is shown in cross section in FIG. 2 and in perspective in FIG. 4. The wineglass member 34 has a stem or lever 35 which projects from a central zone of a bowl portion 36. The bowl portion 36 is hemispheric with smooth, spherical interior and exterior faces. The wineglass member 34 is positioned with the bowl 36 oriented downward within a retainer cup 37. The retainer cup 37 has a cylindrical outer wall, and an inner "top hat" portion 38 also having a cylindrical wall which with the retainer cup wall defines an annular cavity. The rim of the bowl member 36 is retained in this annular cavity. An inner seal ring 39 or annular biasing means is supported on the top hat member 38, while an outer ring seal 40 or annular sealing means is supported on the joystick housing cover 22 against the outer surface of the wine glass member bowl portion 36. The resilient inner ring seal 39 biases the underside of the bowl portion 34 to urge the bowl portion against the outer ring seal 40. The retainer cup 37 is sealed top and bottom to define a sealed cavity containing the joystick mechanism 32. A cone-shaped or frustoconic void or cavity 45 limits the angular travel of the wineglass stem or lever 35.

As shown in FIG. 2, the upper or distal end of the joystick lever 33 fits into a cavity at the lower end of the wineglass member stem 35. This ensures that the x-y travel of the wineglass member will produce corresponding movement of the joystick switch mechanism 32. Electrodes of the joystick switch mechanism 32 are coupled to respective input electrodes of the stepper motors 26, 26. A spring loaded ball assembly 41 is attached to the lower end of the joystick lever 33 and slides on a spherical plate 42 having a conical depression allowing the user to know when the joystick is centered.

The inner and outer seals 39, 40 need to be made of a sealing material such that a good environmental seal is obtained, but as these must be sliding seals, the seal rings 39, 40 must not impose too much resistance against movement of the joystick control 14. In one preferred embodiment, the seal rings 39, 40 can be rings of PTFE, or elastomer-filled PTFE. In an alternative embodiment as shown in FIG. 5, the sealing ring 40' can be "X" shaped in cross section. In a further alternative, as shown in FIG. 6, the ring 40Δ can be a "C" in cross section. Other materials can also be used for the sealing rings.

Also shown in FIG. 2 are video conductors 46 which extend between the modular connector 16 and the tip of the insertion tube 11. Moreover, an illumination fiber optic bundle 47 also extends through the housing, and proceeds distally to the end of the insertion tube and proximally to the connector module.

The joystick mechanism 14 of this invention can be located generally as shown in the preferred embodiment of FIGS. 2 and 3, or can be disposed elsewhere on the control handle 13, without departing from the main principles of this invention.

While the invention has been illustrated and described with respect to a preferred embodiment, it should be understood that the invention is not limited to that precise embodiment. Rather, many modifications and variations would present themselves to those of skill in the art without departing from the scope and spirit of the invention, as defined in the appended claims.

What is claimed is:

1. A video probe comprising an elongated insertion tube that includes an articulated bending section at its distal end, which includes a cable-driven bending mechanism in which at least one pair of cables is moved differentially to bend the articulated bending section, and a control handle which is attached onto a proximal end of the insertion tube, said video probe receiving the at least one pair of cables which pass from the bending mechanism through the insertion tube; said video probe including a housing in which a proximal end of the insertion tube is affixed, actuator means within the housing for differentially moving said at least one pair of control cables, and a joystick control member having a joystick handle protruding from said housing and coupled to said actuator means for moving said control cables in response to manipulation by an operator of said joystick handle; wherein said joystick handle includes a wineglass member having a generally hemispherical bowl portion and a stem portion projecting from said bowl portion; wherein said housing includes an opening through which said stem portion projects and annular sealing means in contact with said bowl portion permitting movement of said wineglass member in two dimensions while sealing said bowl member against infiltration; and an annular resilient ring seal positioned against an underside of said bowl portion opposite said annular sealing means to urge the bowl portion against said sealing means.

2. The video probe of claim 1 wherein said annular sealing means includes a sealing ring of x-shaped cross section.

3. The video probe of claim 1 wherein said annular sealing means includes a sealing ring of c-shaped cross section.

4. The video probe of claim 1 wherein said joystick control member includes an x-y joystick element having a lever projecting into a receptacle in the stem of the wineglass member.

5. The video probe of claim 1 wherein said joystick control member includes a cup member having an outer cylindrical wall and an inner raised top hat portion with a generally cylindrical wall, and said wineglass member bowl portion is positioned with its rim disposed in an annular space defined between said cylindrical walls.

6. The video probe of claim 1 wherein said opening in the housing is cone-shaped void with a frustoconic wall.

7. The video probe of claim 1 wherein said insertion tube includes a rigid tubular member extending from said proximal end thereof distally to said bending section.

* * * * *